United States Patent
Larocca et al.

(10) Patent No.: US 12,396,994 B2
(45) Date of Patent: Aug. 26, 2025

(54) COMPOSITIONS FOR IMPROVING PHYSIOLOGICAL FUNCTION WITH AGE

(71) Applicant: The Regents Of The University Of Colorado, a body corporate, Denver, CO (US)

(72) Inventors: Thomas Larocca, Boulder, CO (US); Douglas Seals, Boulder, CO (US)

(73) Assignee: The Regents Of The University Of Colorado, a body corporate, Denver, CO (US)

( * ) Notice: Subject to any disclaimer, the term of this patent is extended or adjusted under 35 U.S.C. 154(b) by 5 days.

(21) Appl. No.: 16/875,440

(22) Filed: May 15, 2020

(65) Prior Publication Data
US 2020/0276203 A1 Sep. 3, 2020

Related U.S. Application Data

(63) Continuation-in-part of application No. PCT/US2018/061069, filed on Nov. 14, 2018.

(Continued)

(51) Int. Cl.
*A61K 31/522* (2006.01)
*A23L 33/15* (2016.01)
(Continued)

(52) U.S. Cl.
CPC ............ *A61K 31/522* (2013.01); *A23L 33/15* (2016.08); *A61K 31/19* (2013.01); *A61K 31/353* (2013.01);
(Continued)

(58) Field of Classification Search
CPC .... A61K 31/522; A61K 31/19; A61K 31/353; A61K 31/593; A61K 31/7016; A23L 33/15
See application file for complete search history.

(56) References Cited

U.S. PATENT DOCUMENTS 6,410,052 B1 6/2002 Morréet al.
2006/0239987 A1* 10/2006 Foster .................... A23P 20/10
424/94.1

(Continued)

FOREIGN PATENT DOCUMENTS

CN 1843339 10/2006
WO WO 2016/069716 5/2016

OTHER PUBLICATIONS

LifeExtension, Vitamin D3, Retrieved from the Internet on Apr. 26, 2022. (Year: 2022).*

(Continued)

*Primary Examiner* — James H Alstrum-Acevedo
*Assistant Examiner* — Lauren Wells
(74) *Attorney, Agent, or Firm* — LEYDIG, VOIT & MAYER, LTD.

(57) ABSTRACT

Provided are methods for treating a disease or condition associated with reduced autophagy in a patient, which includes administering to the patient, either simultaneously or sequentially, a therapeutically effective amount of a synergistic combination of compounds from at least two and preferably three of the classes of compounds selected from a saccharide, a vitamin, a ketone body, a polyphenol, and a methylxanthine. The compounds may be present in a sub-therapeutic effective amount relative to the compound's dosing when given as a single agent. Also provided are pharmaceutically acceptable compositions and kits including at least two and preferably three of the named classes of compounds.

13 Claims, 5 Drawing Sheets

Related U.S. Application Data

(60) Provisional application No. 62/586,467, filed on Nov. 15, 2017.

(51) Int. Cl.
  A61K 31/19 (2006.01)
  A61K 31/353 (2006.01)
  A61K 31/593 (2006.01)
  A61K 31/7016 (2006.01)

(52) U.S. Cl.
  CPC ........ *A61K 31/593* (2013.01); *A61K 31/7016* (2013.01)

(56) References Cited

U.S. PATENT DOCUMENTS

| | | | |
|---|---|---|---|
| 2014/0363502 A1 | 12/2014 | Sardi | |
| 2015/0104393 A1* | 4/2015 | Zhao-Wilson | A61K 31/5685 424/94.1 |
| 2018/0352843 A1* | 12/2018 | Verburgh | A23L 33/16 |
| 2021/0121489 A1* | 4/2021 | Adlard | A61K 31/7016 |

OTHER PUBLICATIONS

Giuliano et al. AgingSciences, Trehalose. Published Jun. 18, 2014. Retrieved from the Internet on Apr. 20, 2022, hhttps://www.anti-agingfirewalls.com/2014/06/18/trehelose-a-natural-sugar-that-could-possibly-be-consumed-for-health-and-longevity/ (Year : 2014).*

Menard et al. Neuroprotective effects of resveratrol and epigallocatechin gallate polyphenols are mediated by the activation of protein kinase C gamma, Frontiers in Cellular Neuroscience, vol. 7, Published 2013. (Year: 2013).*

M.E. Moore, A. Piazza, Y. McCartney, M.A. Lynch; Evidence that vitamin D3 reverses age-related inflammatory changes in the rat hippocampus. Biochem Soc Trans Aug. 1, 2005; 33 (4): 573-577. (Year: 2005).*

Pervin et al. Blood brain barrier permeability of (-)-epigallocatechin gallate, its proliferation-enhancing activity of human neuroblastoma SH-SY5Y cells, and its preventive effect on age-related cognitive dysfunction in mice. Biochem Biophys Rep. Jan. 5, 2017;9:180-186. (Year: 2017).*

Raman, Ryan. What Vitamin D Dosage is Best? Retrieved from the Internet on Aug. 20, 2024, https://www.healthline.com/nutrition/vitamin-d-dosage. Published Oct. 8, 2017. (Year: 2017).*

Gongora et al. Diet and Nutrition in Dementia and Cognitive Decline. Abstract of Chapter 81-Caffeine Consumption and Prevention of Cognitive Decline: A Focus on Mechanisms, pp. 879-889. Published 2015. (Year: 2015).*

Smit, H., Rogers, P. Effects of low doses of caffeine on cognitive performance, mood and thirst in low and higher caffeine consumers. Psychopharmacology 152, 167-173 (2000). (Year: 2000).*

Wasta. New study sheds light on why cancer often strikes those with healthy lifestyles. Johns Hopkins University HUB. Retrieved from the Internet Aug. 20, 2024. Published Mar. 23, 2017. (Year: 2017).*

Cross, Ryan. One in five 'healthy' adults may carry disease-related genetic mutations. Retrieved from the Internet on Aug. 20, 2024, https://www.science.org/content/article/one-five-healthy-adults-may-carry-disease-related-genetic-mutations. Published Jun. 26, 2017. (Year: 2017).*

Ben-Shlomo et al. (2014) "Aortic pulse wave velocity improves cardiovascular event prediction: an individual participant meta-analysis of prospective observational data from 17,635 subjects," Journal of the American College of Cardiology 63(7): 636-646.

Biederbick et al. (1995) "Monodansylcadaverine (MDC) is a specific in vivo marker for autophagic vacuoles," Eur. J. Cell. Biol. 66:3-14 (Abstract Only).

Chan et al. (2012) "A novel image-based cytometry method for autophagy detection in living cells," Autophagy, 8(9): 1371-1382.

Cooper et al. (2011) "Objective measures of physical capability and subsequent health: a systematic review," Age and Ageing, 40(1): 14-23.

De Brito et al. (2014) "Ability to sit and rise from the floor as a predictor of all-cause mortality" European Journal of Preventive Cardiology 21(7): 892-898.

Ferrari et al. (2011) "Diet-derived phytochemicals: from cancer chemoprevention to cardio-oncological prevention," Current Drug Targets, 12(13):1909-1924.

Fleenor et al. (2012) "Superoxide-lowering therapy with TEMPOL reverses arterial dysfunction with aging in mice," Aging Cell, 11(2): 269-276.

Fontana et al. (2013) "Aging promotes the development of diet-induced murine steatohepatitis but not steatosis," Hepatology, 57(3): 995-1004.

Galis et al. (2013) "National Heart, Lung, and Blood Institute and the Translation of Cardiovascular Discoveries Into Therapeutic Approaches," Circulation Research, 112(9): 1212-1218.

Galluzzi et al. (2012) "Autophagy Mediates the Metabolic Benefits of Endurance Training," Circulation Research, 110(10): 1276-1278.

Gregg et al. (2012) "A mouse model of accelerated liver aging caused by a defect in DNA repair," Hepatology, 55(2): 609-621.

Hannigan et al. (2009) "Macroautophagy: the key ingredient to a healthy diet?" Autophagy, 5(2): 140-51.

Ingram et al. (2006) "Calorie restriction mimetics: an emerging research field," Aging Cell, 5(2): p. 97-108.

International Search Report and Written Opinion, mailed Jan. 24, 2019, in corresponding International Application No. PCT/US2018/061069, 11 pp.

Justice et al. (2013) "Battery of behavioral tests in mice that models age-associated changes in human motor function," Age (Dordr), 36:583-595.

Kirkland (2013) "Translating advances from the basic biology of aging into clinical application," Experimental Gerontology 48(1): p. 1-5.

Klionsky et al. (Jan. 2016) "Guidelines for the use and interpretation of assays for monitoring autophagy," Autophagy. 12(1): 1-222.

Komatsu et al. (2005) "Impairment of starvation-induced and constitutive autophagy in Atg7-deficient mice," J Cell Biol. 169:425-434.

Lakatta et al. (2003) "Arterial and cardiac aging: major shareholders in cardiovascular disease enterprises: Part I: aging arteries: a "set up" for vascular disease," Circulation, 107(1): 139-146.

LaRocca et al. (2012) "Translational evidence that impaired autophagy contributes to arterial ageing," The Journal of Physiology 590(14): 3305-3316.

LaRocca et al. (2013) "The autophagy enhancer spermidine reverses arterial aging," Mech Ageing Dev, 134(7-8): 314-320.

Larrick et al. (2010) "Applied Healthspan engineering," Rejuvenation Research, 13(2-3): 265-280.

Liu et al. (2012) "Identification of an annonaceous acetogenin mimetic, AA005, as an AMPK activator and autophagy inducer in colon cancer cells," PloS one 7(10): e47049.

Lunenfeld et al. (2013) "The clinical consequences of an ageing world and preventive strategies," Best Practice & Research Clinical Obstetrics & Gynaecology, 27(5): 643-659.

Mitchell et al. (2010) "Arterial stiffness and cardiovascular events: the Framingham Heart Study," Circulation, 121(4): 505-511.

Mizushima et al. (2011) "Autophagy: Renovation of Cells and Tissues," Cell, 147(4): 728-741.

Morselli et al. (2011)"Spermidine and resveratrol induce autophagy by distinct pathways converging on the acetylproteome," The Journal of Cell Biology 192(4): 615-629.

Nicoletti (2012) "Nutraceuticals and botanicals: overview and perspectives," International Journal of Food Sciences and Nutrition, 63(S1): 2-6 (Abstract Only).

Olshansky et al. (2009) "Aging in America in the twenty-first century: demographic forecasts from the MacArthur Foundation Research Network on an Aging Society," Milbank Quarterly, 87(4): 842-862.

Pallauf et al. (2012) "Autophagy, polyphenols and healthy ageing," Ageing Res Rev, 12(1): 237-252 (Abstract Only).

(56) References Cited

OTHER PUBLICATIONS

Pandit et al. (2011) "FoxM1 knockdown sensitizes human cancer cells to proteasome inhibitor-induced apoptosis but not to autophagy," Cell Cycle, 10(19): 3269-3273.

Pietrocola et al. (2012) "Pro-autophagic polyphenols reduce the acetylation of cytoplasmic proteins," Cell Cycle, 11(20), 3851-3860.

Reuben et al. (2013) "Motor assessment using the NIH Toolbox," Neurology, 80 (Suppl 3): S65-75.

Rubinsztein et al. (2011) "Autophagy and Aging," Cell, 146(5): 682-695.

Sasaki et al. (2007) "Grip strength predicts cause-specific mortality in middle-aged and elderly persons," The American Journal of Medicine, 120(4): 337-342 (Abstract Only).

Seals et al. (2011) "Aging and vascular endothelial function in humans," Clin Sci (Lond), 120(9): 357-375.

Sheedfar et al. (2013) "Liver diseases and aging: friends or foes?" Aging Cell, 12, 950-954.

Singletary et al. (2008) "Diet, autophagy, and cancer: a review," Cancer Epidemiology, Biomarkers & Prevention, 17(7): 1596-1610.

Sudarsanam et al. (2010) "Functional consequences of mTOR inhibition," Curr Opin Drug Discov Devel, 13(1): 31-40.

Sui et al. (2007) "Estimated functional capacity predicts mortality in older adults," Journal of the American Geriatrics Society 55(12): 1940-1947.

Teumer et al. (2016) "Genomewide meta-analysis identifies loci associated with IGF-I and IGFBP-3 levels with impact on age-related traits," Aging Cell, 15: 811-824.

Wohlgemuth et al. (2010) "Skeletal muscle autophagy and apoptosis during aging: Effects of calorie restriction and life-long exercise," Experimental Gerontology, 45(2): 138-148.

Zhang et al. (2008) "Restoration of chaperone-mediated autophagy in aging liver improves cellular maintenance and hepatic function," Nature Medicine, 14(9): 959-965.

Bhoora et al. (2020), "Cholecalciferol inhibits cell growth and induces apoptosis in the CaSki cell line," Medical Sciences, 8(1): 12.

Chen et al. (2016), "Trehalose, sucrose and raffinose are novel activators of autophagy in human keratinocytes through an mTOR-independent pathway," Scientific reports, 6(1): 1-17.

Kim et al. (2013), "Epigallocatechin Gallate (EGCG) Stimulates Autophagy in Vascular Endothelial Cells," Journal of Biological Chemistry, 288(31): 22693-22705.

Abokyi et al. (2020), "Autophagy upregulation by the TFEB inducer trehalose protects against oxidative damage and cell death associated with NRF2 inhibition in human RPE cells," Oxidative Medicine and Cellular Longevity, Article ID 5296341.

Baulieu, Etienne-Emile (1996), "Dehydroepiandrosterone (DHEA): A Fountain of Youth?," J. Clinical Endocrinology and Metabolism, 81(9): 3147-3151.

Baulieu, Etienne-Emile (2000), "Dehydroepiandrosterone (DHEA), DHEA sulfate, and aging: Contribution of the DHEAge Study to a sociobiomedical issue," PNAS, 97(8): 4279-4284.

Xiong et al. (2021), "1α,25-Dihydroxyvitamin D3 promotes angiogenesis by alleviating AGEs-induced autophagy," Arch. BioChem. Biophys., 712:109041 (Abstract only).

Yuk et al. (2009), "Vitamin D3 Induces Autophagy in Human Monocytes/Macrophages via Cathelicidin," Cell Host & Microbe, 6: 231-243.

Zhou et al. (2014), "Epigallocatechin-3-gallate (EGCG), a green tea polyphenol, stimulates hepatic autophagy and lipid clearance," PloS one, 9(1): e87161.

* cited by examiner

COMPOSITIONS FOR IMPROVING PHYSIOLOGICAL FUNCTION WITH AGE

CROSS-REFERENCE TO RELATED APPLICATIONS

This application is a continuation-in-part application claiming priority to International Application No. PCT/US18/61069, filed Nov. 14, 2018, which claims the benefit of U.S. Provisional Patent Application No. 62/586,467 filed Nov. 15, 2017, all of which are specifically incorporated by reference to the extent not inconsistent herewith.

STATEMENT REGARDING FEDERALLY SPONSORED RESEARCH OR DEVELOPMENT

This invention was made with government support under grant numbers AG013038 and AG039210, awarded by the National Institutes of Health. The government has certain rights in the invention.

BACKGROUND OF INVENTION

Aging causes numerous adverse changes in physiology, including arterial dysfunction, reduced motor function (strength, locomotion, etc.) and impaired liver/metabolic function. Collectively, these changes reduce independence and quality of life and predispose older adults to disabilities and chronic diseases. Because the number of older adults in the US is expected to more than double by 2050, age-related physiological dysfunction (and resulting diseases/disabilities) are expected to cause major socio-economic problems in the near future. Identifying novel therapies that improve physiological function with aging is, therefore, an important biomedical research objective.

Because aging is a complex process with numerous physiological consequences, agents that target fundamental "upstream" causes of aging (rather than treating isolated late-life pathologies as pharmaceuticals do) may have the greatest probability of reversing dysfunction and preventing the development of disease. In this context, autophagy is a particularly promising target. Autophagy is the major cellular process for recycling damaged proteins and organelles, and it protects many cellular and systemic physiological functions against aging and disease. Impaired autophagy is implicated in numerous age-related disorders-including vascular dysfunction, impaired motor (neuromuscular) function and altered liver structure/function-all of which contribute significantly to disability and disease. Thus, the development of autophagy-enhancing therapies is a compelling direction for research aimed at preventing/treating disorders of aging.

Unfortunately, many pharmacological autophagy inducers have off-target effects (e.g., rapamycin). As a result, there is considerable interest in nutraceuticals-naturally occurring, bioactive food compounds—that promote autophagy. We and others have shown that dietary supplementation with autophagy-enhancing nutraceuticals, such as the carbohydrate trehalose, reverses age-related dysfunction, but there are limitations to this approach. For example, the amount of trehalose that improves function in mice equates to >500 calories of sugar per day in humans. The same is true for many nutraceuticals; the concentrations needed for beneficial effects are often supraphysiological.

It would therefore be desirable to develop formulations of naturally occurring, bioactive food compounds with significantly lowered dosages of each compound, while still maintaining a therapeutic level of effectiveness for enhancing autophagy.

SUMMARY OF THE INVENTION

In the present invention, combinations and formulations of naturally occurring, bioactive food compounds with significantly lowered dosages of each compound were found that were able to achieve effects similar to trehalose and other autophagy inducers. The present inventors were able to develop synergistic combinations of naturally occurring; bioactive food compounds which were able to achieve therapeutic effects at far lower dosages than dosages used by the single agents. Such formulations, in some embodiments, are called "autophagy-enhancing optimized nutraceutical (AEON), which can be understood as formulations of naturally occurring dietary compounds that enhance autophagy via the synergistic action of low doses of its ingredients.

The present inventors conducted in vitro screening experiments to identify combinations of nutraceutical compounds that synergistically induce autophagy, which were then developed into promising combinations of FDA-approvable food supplements, and they tested the combinations in vivo in a mouse model of physiological aging.

In one embodiment the present invention includes a method for treating a disease or condition associated with reduced autophagy in a patient, comprising administering to said patient simultaneously or sequentially a therapeutically effective amount of a combination comprising at least two compounds, at least three compounds, at least four compounds, or at least five compounds independently selected from at least two of the following groups: a saccharide, a vitamin, a ketone body, a polyphenol, and a methylxanthine, or pharmaceutically acceptable salts thereof, wherein the combination has a synergistic autophagy enhancement effect. The compounds may each individually be capable of enhancing autophagy; wherein each compound in the combination may be present in a subtherapeutic effective amount relative to the compound's dosing when given as a single agent.

The saccharide may include trehalose, sucrose, maltose, lactulose, melibiose, and raffinose; the ketone body compound may include 13-hydroxybutyrate and acetoacetate; the polyphenol may include kaempferol, quercetin, myricitin, resveratrol, or a catechin such as (−)-epicatechin, (−)-epicatechin gallate, (−)-gallocatechin gallate, (−)-epigallocatechin and/or (−)-epigallocatechin gallate; the vitamin may include cholecalciferol, ascorbic acid, phylloquinone, menaquinone, cobalamin, and niacin; and the methylxanthine may include caffeine, aminophylline, 3-isobutyl-1-methylxanthine (IBMX), paraxanthine, pentoxifylline, theobromine, and theophylline. In some embodiments, the composition includes trehalose, cholecalciferol, and 13-hydroxybutyrate; or includes trehalose, cholecalciferol, and epigallocatechin gallate; or includes caffeine, epigallocatechin gallate, and 13-hydroxybutyrate, where each individual compound is present at a subtherapeutic amount as compared to the dosage of the compound as a single agent. The combinations may be orally administered.

The disease or condition associated with reduced autophagy may include aging, cardiovascular disease, neurodegenerative disease, or inflammatory disease and aging may include increased arterial stiffness, reduced arterial endothelial function, reduced endurance, reduced muscle strength, reduced muscle coordination, and increased hepatic cell damage.

The invention also includes pharmaceutical compositions and kits comprising the compounds disclosed herein in the amounts and combinations disclosed herein.

In an aspect, the invention provides a method for prevent or treating cancer in a patient, comprising administering to the patient simultaneously or sequentially a therapeutically effective amount of a combination comprising at least two compounds independently selected from at least two of the following groups: a saccharide, a vitamin, a ketone body, a polyphenol, and a methylxanthine, or pharmaceutically acceptable salts thereof, wherein the combination has a synergistic cancer treatment effect. In an embodiment, for example, the method is for treating a type of cancer selected from the group consisting of a lymphoma, a melanoma, a glioma, a carcinoma and a malignancy of the CNS. In an embodiment, for example, the method is for treating a type of cancer selected from the group consisting of a carcinoma of the lung, bladder, kidney, ovary, breast, prostate, stomach, and pancreas. In an embodiment, for example, the method is for treating a type of cancer selected from the group consisting of Kaposi's sarcoma, glioblastoma multiforme, and mantle cell lymphoma. In an embodiment, for example, the method is for preventing the onset of the cancer in the patient. In an embodiment, for example, the method is for treating the patient diagnosed with cancer. In an embodiment, for example, the method is for of reducing progression of the cancer in the patient. In an embodiment, for example, the method is for reducing the extent of or eliminating of the cancer in the patient. In an embodiment, for example, the method is for preventing the reoccurrence of the cancer in the patient.

In an aspect, the invention provides a kit comprising a pharmaceutical composition comprising a therapeutically effective amount of a combination comprising at least two compounds independently selected from the group consisting of a saccharide compound, a vitamin compound, a ketone body compound, a polyphenol compound, and a methylxanthine compound, wherein the composition has a synergistic cancer treatment effect.

In an aspect, the invention provides a method for prevent or treating a chronic human disease in a patient, comprising administering to the patient simultaneously or sequentially a therapeutically effective amount of a combination comprising at least two compounds independently selected from at least two of the following groups: a saccharide, a vitamin, a ketone body, a polyphenol, and a methylxanthine, or pharmaceutically acceptable salts thereof, wherein the combination has a synergistic treatment effect for the chronic human disease. In an embodiment, for example, the chronic human disease is selected from the group consisting of a cardiovascular disease, a neurodegenerative disease, Type 2 diabetes and an autoimmune disorder. In an embodiment, for example, the chronic human disease is selected from the group consisting of Alzheimer's disease and Parkinson's disease. In an embodiment, for example, the chronic human disease is selected from the group consisting of rheumatoid arthritis, psoriasis and multiple sclerosis.

In an aspect, the invention provides a kit comprising a pharmaceutical composition comprising a therapeutically effective amount of a combination comprising at least two compounds independently selected from the group consisting of a saccharide compound, a vitamin compound, a ketone body compound, a polyphenol compound, and a methylxanthine compound, wherein the composition has a synergistic treatment effect for the chronic human disease.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1A:
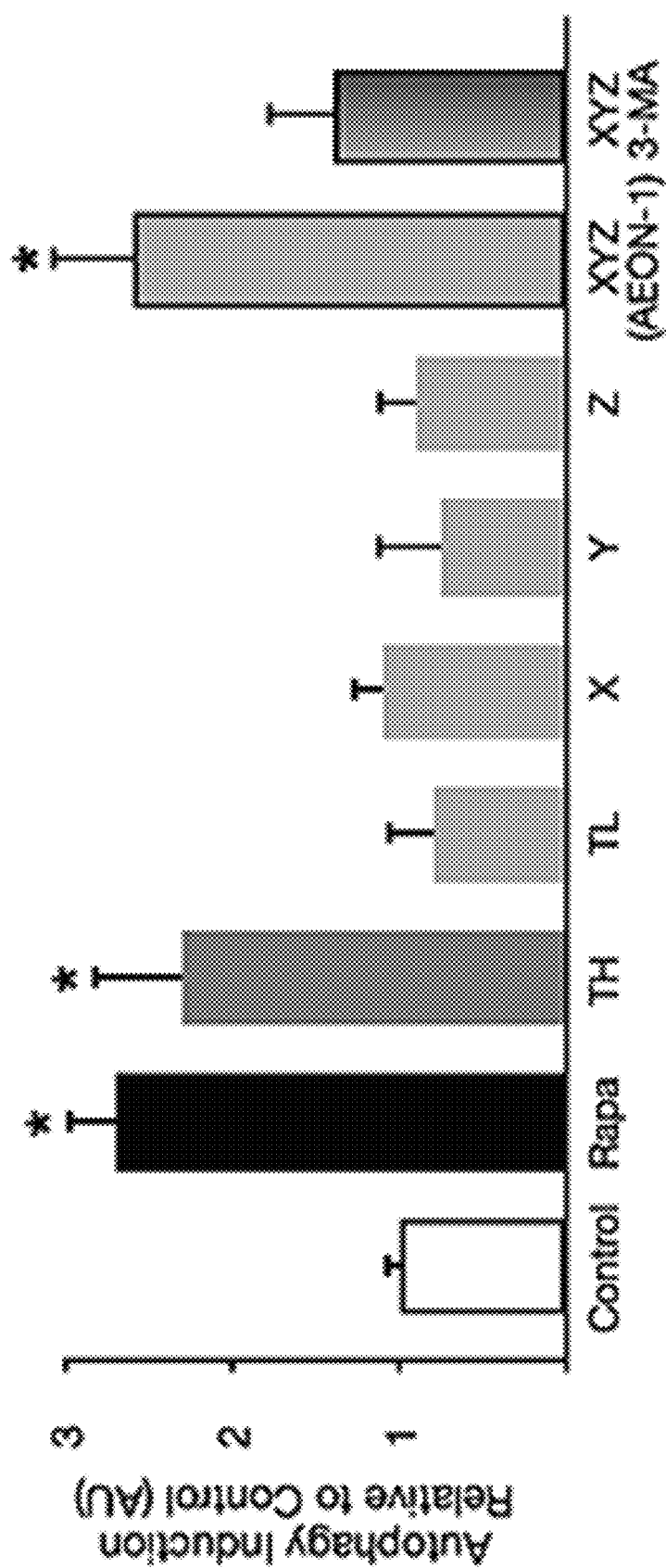
FIG. 1A. Autophagy induction (relative microplate fluorescence) in human umbilical vein endothelial cells (HUVEC) treated for 24 h with rapamycin (rapa), high dose trehalose (TH), low dose trehalose (TL), the ingredients X, Y and Z alone and or in combination with/without the autophagy inhibitor 3-MA (10 mM).

In general, the terms and phrases used herein have their art-recognized meaning, which can be found by reference to standard texts, journal references and contexts known to those skilled in the art. The following definitions are provided to clarify their specific use in the context of the invention.

Autophagy is a process by which cells degrade their own components, recycling amino acids and other building blocks that can be reused. Such degradation is performed by lysosomal acidic hydrolases. During autophagy, double-membrane vesicular structures named autophagosomes are formed and cytosolic components are delivered to the lysosome for breakdown. The autophagy machinery is conserved among eukaryotes from yeast to humans and plays an important role in maintaining cellular homeostasis despite exposure to various types of environmental damage. Abnormal autophagy has been found in many human disorders, including neurodegenerative diseases, metabolic disease, infections and cancer. Accordingly, pharmacological approaches targeted to activate or inhibit autophagy are currently obtaining attention for the treatment of these diseases. Interestingly, trehalose has been identified as an inducer of autophagy in neural cells.

Autophagy is a tightly regulated process that plays an important role in normal cell growth, development, and homeostasis, helping to maintain a balance between the synthesis, degradation, and subsequent recycling of cellular products. It is a major mechanism by which starving cells can reallocate nutrients from less-essential processes to more essential processes. During nutrient starvation, increased levels of autophagy lead to the breakdown of non-vital components and the release of nutrients, ensuring that vital processes can continue. Mutant yeast cells that have a reduced autophagic capability rapidly perish in nutrient-deficient conditions. A gene known as Atg7 has been implicated in nutrient-mediated autophagy, and studies in mice have shown that starvation-induced autophagy was impaired in Atg7-deficient mice. Komatsu M et al. (2005) J Cell Biol. 169:425-434. Three types of autophagy can be distinguished, depending on the pathway along which cellular components are delivered to lysosomes: macroautophagy, microautophagy, and chaperone-mediated autophagy (CMA). The present invention, when referring to "autophagy" can refer to one or more of these types of autophagy.

Autophagy degrades damaged organelles, cell membranes, and proteins. The failure of autophagy is thought to be an important factor in the accumulation of cell damage and, therefore, aging. Multiple reports indicate that proteins required for autophagy induction, such as sirtuin 1, have reduced expression in aged tissues; levels of autophagy have been shown to diminish with age. Reduced levels of autophagy have also been associated with obesity, diabetes, cancer, neurodegenerative diseases, cardiovascular disease, osteoarthritis, and age-related macular degeneration.

In certain embodiments, the invention provides methods of increasing or enhancing autophagy, both in vivo and in vitro, and/or methods of treating or preventing various diseases and conditions using the compositions disclosed herein. In particular embodiments, a disease or disorder treated or prevented according to the present invention is a disease or disorder associated with reduced autophagy, or which would benefit from increased autophagy, including but not limited to any of the diseases and conditions described herein.

An aspect of the invention is a method of treating or preventing a disease or condition associated with, or characterized by, reduced or decreased autophagy, or which would benefit from increased autophagy. Such disease or condition includes preventing or treating cardiovascular disease, preventing or treating cancer, preventing or treating macular degeneration, treating, attenuating or preventing diseases or conditions associated with aging, and other conditions and illnesses, including the incidence or severity of neurodegenerative diseases such as Alzheimer's Disease and Parkinson's Disease, and anti-inflammatory activity. The condition associated with reduced or decreased autophagy may include decreased physiological function, such as decreased vascular function, indicated by conditions such as increased arterial stiffness and reduced arterial endothelial function; reduced or impaired motor (neuromuscular function) such as reduced endurance, reduced muscle strength and coordination; reduced liver structure/function, such as increase in cellular damage that impairs the ability of the liver to respond to metabolic and other hepatic insults and increases the risk of liver disease.

As used herein, unless the context makes clear otherwise, "treat," and similar words such as "treatment," "treated," "treating," etc., indicates an approach for obtaining beneficial or desired results, including clinical results. Treatment can involve optionally either the reduction or amelioration of symptoms of the disease or condition, or the delaying of the progression of the disease or condition. In some embodiments, treatment is achieved by reducing the duration of the disease or condition. Administration of a compound described herein may, in some embodiments, treat one or more of such symptoms.

As used herein, unless the context makes clear otherwise, "prevent," and similar words such as "prevention," "prevented," "preventing," etc., indicates an approach for preventing, inhibiting, or reducing the likelihood of the onset or recurrence of a disease or condition. It also refers to preventing, inhibiting, or reducing the likelihood of the occurrence or recurrence of the symptoms of a disease or condition, or optionally an approach for delaying the onset or recurrence of a disease or condition or delaying the occurrence or recurrence of the symptoms of a disease or condition. As used herein, "prevent" and similar words also includes reducing the intensity, effect, symptoms or burden of a disease or condition prior to onset or recurrence of the disease or condition.

An increase in autophagy in a cell can be measured using any suitable assay for measuring autophagy. For example, autophagy formation can be determined by using the fluorescent dye monodansylcadaverine (MDC) (Sigma-Aldrich, 30432). This dye selectively labels autophagic vacuoles. (Biederbick A et al. (1995) Eur. J. Cell. Biol. 66:3-14.) Autophagy may also be determined by examining the change in the ratio of the proteins involved in autophagy, such as LC3-II to LC3-I, for example, using Western blot analysis. With such a method, an increase in the LC3-II/LC3-I ratio in a treated cell above the baseline, untreated cells LC3-II/LC3-I ratio, would be considered as an increase in autophagy. Examination of other protein levels such as p62 may also help in the confirmation. For the purposes of calculating the percent (%) increase in autophagy in a cell, the ratio of LC3-II/LC3-I at baseline (B-Ratio) and the ratio of LC3-II/LC3-I during treatment (T-Ratio) may be employed. The percent (%) increase can be determined mathematically, for example, by the formula $100 \times [((T\text{-Ratio}) - (B\text{-Ratio}))/(B\text{-Ratio})]$.

Autophagy is said to be increased in a cell if it is measurably greater than autophagy that is or would be present in an untreated or placebo control cell. In one embodiment autophagy is said to be increased in a cell if it is greater by a statistically significant amount or degree than autophagy that is or would be present in an untreated or placebo control cell. In certain embodiments, the increase in autophagy is an increase of at least 5%, at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, at least 400%, at least 500%, at least 600%, at least 700%, at least 800%, at least 900%, at least 1,000% or greater than 1,000%, as compared to the level of autophagy present in an untreated cell or a cell treated with a placebo.

In certain embodiments, the increase in autophagy is an increase of 5-500%, 10-500%, 15-500%, 20-500%, 25-500%, 30-500%, 40-500%, 50-500%, 60-500%, at least 70-500%, 80-500%, 90-500%, 100-500%, 150-500%, 200-500%, 300-500%, or 400-500%, 5-1,000%, 10-500%, 15-1,000%, 20-1,000%, 25-1,000%, 30-1,000%, 40-1,000%, 50-1,000%, 60-1,000%, at least 70-1,000%, 80-1,000%, 90-1,000%, 100-1,000%, 150-1,000%, 200-1,000%, 300-1,000%, 400-1,000%, 500-1,000%, 600-1,000%, 700-1, 000%, 800-1,000% or 900-1,000%, as compared to the level of autophagy present in an untreated cell or a cell treated with a placebo.

As set forth in greater detail in the examples herein, combination therapy using at least two, or at least three, different compounds, such as naturally occurring, bioactive food compounds, have been tested in cells for efficacy in enhancing autophagy and in mouse models of aging for efficacy in delaying onset of aging-mediated decline. Surprisingly, the inventors found that combinations of at least two, or at least three, different compounds from the categories named herein was significantly more effective, and in some embodiments, synergistic, at enhancing autophagy in cells and/or in delaying onset of aging-mediated decline in mice, compared to control groups and single compound alone groups.

In one embodiment, the present invention includes a method for treating a disease or condition associated with reduced autophagy in a patient, comprising administering to said patient simultaneously or sequentially a therapeutically effective amount of a combination comprising at least two compounds independently selected from at least two of the following groups: a saccharide, a vitamin, a ketone body, a polyphenol, and a methylxanthine, or pharmaceutically acceptable salts thereof, wherein the combination has a synergistic autophagy enhancement effect.

The method of treatment, the compositions, and/or the compositions may each individually comprise, consist essentially of, or consist of the compounds and combinations named herein.

And as used herein, "synergy" or "synergistic" refers to cooperation or cooperating for an enhanced effect such that the working together of two or more things produces a total effect greater than the sum of their individual effects, as compared to "antagonistic," which is used to especially describe interactions of drugs that counteract or neutralize each other's effect. As used herein, "autophagy enhancer" is meant to refer to a composition that increases the level of autophagy in a cell in its presence compared to the level of autophagy in a cell in its absence. As used herein "cancer treatment effect" refers to a therapeutic effect in the context of the treatment or prevention of cancer, including preventing the onset of cancer in a patient, reducing progression of cancer in a patient, reducing the extent of or eliminating of cancer in a patient and/or preventing the reoccurrence of cancer in a patient.

In an embodiment, the methods provide a synergistic autophagy enhancement effect of at least 2-fold or greater, optionally for some embodiments, at least 10-fold or greater, as compared to the aggregate of the individual effects of the compounds as administered separately. In an embodiment, the methods provide a synergistic cancer treatment effect of at least 10% inhibition of proliferation or greater, optionally for some embodiments, at least 50% inhibition of proliferation or greater, as compared to the aggregate of the individual effects of the compounds as administered separately.

Synergy can be detected, identified and/or quantitated by methods as known in the art. Example approaches for detecting, identifying and/or quantitating synergy include to measure: autophagic flux, conversion of LC3-i to LC3-ii, autophagosome accumulation, post-translational modification of autophagic proteins, autophagic protein expression, autophagic target protein degradation, lysosomal turnover. Example methods for detecting, identifying and/or quantitating synergy in the context of autophagy enhancement are described in Klionsky, Daniel J., et al. "Guidelines for the use and interpretation of assays for monitoring autophagy." Autophagy12.1 (2016): 1-222.

The following references also provide examples of synergistic autophagy and cancer inhibition inducers using some of the methods listed above: (i) Morselli, Eugenia, et al. "Spermidine and resveratrol induce autophagy by distinct pathways converging on the acetylproteome." The Journal of cell biology 192.4 (2011): 615-629. (ii) Liu, Yong-Qiang, et al. "Identification of an annonaceous acetogenin mimetic, AA005, as an AMPK activator and autophagy inducer in colon cancer cells." PloS one 7.10 (2012): e47049.

In other embodiments, the combination comprises at least three compounds, at least four compounds, at least five compounds or more independently selected from at least three, at least four, at least five or more, respectively, of the following groups: a saccharide, a vitamin, a ketone body, a polyphenol, and a methylxanthine, or pharmaceutically acceptable salts thereof, wherein the combination has a synergistic autophagy enhancement effect.

In an embodiment, each compound in the combination is given in a subtherapeutically effective amount relative to the compound's dosing when given as a single agent. For example, the amount and or dosage of each compound in the combination may be less than 50%, less than 40%, less than 30%, less than 20%, less than 15%, less than 10%, less than 8%, less than 6%, less than 4%, less than 2%, or less than 1% of the compound's dosing when given as a single agent.

In many cases, the individual compounds listed herein as part of the inventive compositions and/or combinations have been reported to induce autophagy, for example, in cell-based assays, as single agents, at concentrations greater than is practical to use for therapeutic purposes in humans or animals. For example, trehalose induces autophagy in cells and in mice when used at 50-100 mM concentrations. Extrapolated to humans on a per kilogram basis, such amounts would include about 100-200 g trehalose per day. Such amounts of trehalose are undesirable for administration to a patient, as this would result in a sugar intake of about 400-800 calories per day, which can result in side effects such as weight gain and gastrointestinal discomfort (Kaplan et al., AGING 2016). Similarly, caffeine is reported to induce autophagy at 1-20 mM concentrations, however, such amounts are about 100-fold greater than the blood levels of caffeine achieved by drinking several cups of coffee.

In embodiments, the invention includes wherein the saccharide compound, the vitamin compound, the ketone body compound, the polyphenol compound, and the methylxanthine compound are each independently capable of enhancing autophagy.

According to the invention, a saccharide includes a saccharide compound that is capable of enhancing autophagy, either alone as a single agent or as part of an inventive combination as disclosed herein. Appropriate saccharides include, for example, trehalose, sucrose, maltose, lactulose, melibiose, and/or raffinose. Trehalose is a natural disaccharide that is found in a diverse range of organisms, such as plants, bacteria, yeast and fungi, however, mammalian cells cannot synthesize trehalose. Trehalose, also known as mycose or tremalose, is a natural alpha-linked disaccharide formed by an α,α-1,1-glucoside bond between two a-glucose units.

Accordingly, the amount of the saccharide compound to use includes between about 1% and about 50% of the therapeutic dose as a single agent, or between about 5% and about 50% of the therapeutic dose as a single agent, or between about 10% and about 50% of the therapeutic dose as a single agent, or about 10% of the dose of the therapeutic dose as a single agent. For example, the saccharide, in the combination, the saccharide can be used in a formulation between about 0.1 mM and about 100 mM; between about 0.5 mM and about 80 mM, between about 1 mM and about 50 mM; between about 2 mM and about 30 mM; between about 3 mM and about 20 mM; between about 4 mM and about 20 mM; between about 5 mM and about 10 mM. Alternatively, the saccharide can be administered, in a human, at the following dose ranges. The dose ranges are given for trehalose, but one of skill in the art can adjust the dosing for other saccharides so the equivalent amount is given. In embodiments, the dose ranges are between about 0.1 g and about 100 g per day; between about 0.5 g and about 80 g per day; between about 1 g and about 60 g per day; between about 1.5 g and about 40 g per day; between about 2 g and about 20 g per day; between about 2.5 g and about 10 g per day; between about 3 g and about 5 g per day. Alternatively, in relation to a 68 kg person, in an amount of between about 0.10 mg/kg to about 500 mg/kg per day; between about 0.50 mg/kg and about 200 mg/kg per day, between about 1 mg/kg and about 150 mg/kg per day; or between about 5 mg/kg and about 120 mg/kg per day, between about 10 mg/kg and about 100 mg/kg per day; or between about 20 mg/kg and about 80 mg/kg per day; between about 30 mg/kg and about 70 mg/kg per day; or between about 35 mg/kg and about 68 mg/kg per day. In embodiments, amounts of the saccharide to administer to a human are 5 mM or 10 mM, 2-4 g per day, or 33 or 66 mg/kg/day.

According to the invention, a vitamin includes a vitamin compound that is capable of enhancing autophagy, either alone as a single agent or as part of an inventive combination disclosed herein. The vitamin may be cholecalciferol, ascorbic acid, phylloquinone, menaquinone, cobalamin, and/or niacin. In one embodiment, the vitamin is vitamin D. Vitamin D refers to a group of fat-soluble secosteroids responsible for increasing intestinal absorption of calcium, magnesium, and phosphate, and multiple other biological effects. In humans, the most important compounds in this group are vitamin D3 (also known as cholecalciferol) and vitamin D2 (ergocalciferol). The hormonally active form of vitamin D (VD), 1,25-dihydroxycholecalciferol, has well-established actions on autophagy and has low toxicity at low concentrations (<1,000 µg/day).

Accordingly, the amount of the vitamin to use includes between about 1% and about 50% of the therapeutic dose as a single agent, or between about 5% and about 50% of the therapeutic dose as a single agent, or between about 10% and about 50% of the therapeutic dose as a single agent, or about 10% of the dose of the therapeutic dose as a single agent. For example, the vitamin, in the combination, can be used in a formulation of between about 0.1 nM and about 50 nM; between about 0.5 nM and about 20 nM, between about 1 nM and about 10 nM; between about 1.5 nM and about 5 nM; between about 2 nM and about 3 nM. Alternatively, the vitamin can be administered, in a human, at the following dose ranges. The dose ranges are given for cholecalciferol, but one of skill in the art can adjust the dosing for other vitamins so the equivalent amount is given. In embodiments, the dose ranges are between about 0.1 µg and about 100 µg per day; between about 0.5 µg and about 90 µg per day; between about 1 µg and about 80 µg per day; between about 1.5 µg and about 70 µg per day; between about 2 µg and about 50 µg per day; or, alternatively, in relation to a 60 kg person, in an amount of between about 1 ng/kg to about 500 ng/kg per day; between about 5 ng/kg and about 400 ng/kg per day, between about 10 ng/kg and about 300 ng/kg per day; between about 20 ng/kg and about 200 ng/kg per day, between about 20 ng/kg and about 100 ng/kg per day. In embodiments, amounts of the vitamin to administer to a human are either 2 nM, 1.6 µg per day, or 26 ng/kg/day.

According to the invention, a polyphenol includes a polyphenol that is capable of enhancing autophagy, either alone as a single agent or as part of an inventive combination disclosed herein. Illustrative polyphenol compounds include, but are not limited to, pterostilbene, resveratrol, TMS (3,4',5-trans-trimethyoxystilbene), 3,4',4-DH-5-MS (3,4'-dihydroxy 5-methoxy-trans-stilbene), 3,5-DH-4'MS (3,5-dihydroxy-4'-,ethoxy-trans-stilbene), kaempferol, myricitin, a catechin, including but not limited to (−)-epicatechin, (−)-epicatechin gallate, (−)-gallocatechin gallate, (−)-epigallocatechin and (−)-epigallocatechin gallate; a phenolic acid, including but not limited to gallic acid, caffeic acid and ellagic acid; a bioflavanoid, including but not limited to an anthocyanin, apigenin, and quercetin; and a complex polyphenol, including but not limited to, a tannin and a lignan, and any combination thereof.

Accordingly, the amount of the polyphenol to use includes between about 1% and about 50% of the therapeutic dose as a single agent, or between about 5% and about 50% of the therapeutic dose as a single agent, or between about 10% and about 50% of the therapeutic dose as a single agent, or about 10% of the dose of the therapeutic dose as a single agent. For example, the polyphenol, in the combination, can be used in a formulation of between about 0.01 µM and about 50 µM; between about 0.1 µM and about 20 µM, between about 0.5 µM and about 5 µM; between about 1 µM and about 2 µM. Alternatively, the polyphenol can be administered, in a human, at the following dose ranges. The dose ranges are given for epigallocatechin, but one of skill in the art can adjust the dosing for other polyphenols so the equivalent amount is given. The polyphenol can be administered at between about 0.01 mg and about 200 mg per day; between about 0.05 mg and about 100 mg per day; between about 0.1 mg and about 100 mg per day; between about 0.2 mg and about 100 mg per day; between about 0.3 mg and about 50 mg per day. Alternatively, in relation to a 60 kg person, in an amount of between about 0.1 µg/kg to about 400 µg/kg per day; between about 0.5 µg/kg and about 300 µg/kg per day, between about 1 µg/kg and about 200 µg/kg per day; between about 2 µg/kg and about 100 µg/kg per day; between about 3 µg/kg and about 50 µg/kg per day. In embodiments, amounts of the polyphenol to administer to a human are either 1 µM, 240 µg per day, or 4 µg/kg/day.

According to the invention, a ketone body includes a ketone body that is capable of enhancing autophagy, either alone as a single agent or as part of an inventive combination disclosed herein. Illustrative ketone bodies include β-hydroxybutyrate, acetoacetate, acetone and combinations thereof. It is known that the liver can metabolize and cause interchange between β-hydroxybutyrate and acetoacetate in vivo.

Accordingly, the amount of the ketone body to use includes between about 1% and about 50% of the therapeutic dose as a single agent, or between about 5% and about 50% of the therapeutic dose as a single agent, or between about 10% and about 50% of the therapeutic dose as a single agent, or about 10% of the dose of the therapeutic dose as a single agent. For example, the ketone body, in the combination, can be used in a formulation of between about 0.01 µM and about 50 µM; between about 0.1 µM and about 20 µM, between about 0.5 µM and about 5 µM; between about 1 µM and about 2 µM. Alternatively, the ketone body can be administered, in a human, at the following dose ranges. The dose ranges are given for β-hydroxybutyrate, but one of skill in the art can adjust the dosing for other ketone bodies so the equivalent amount is given. The ketone body can be administered at between about 1 mg and about 400 mg per day; between about 10 mg and about 400 mg per day; between about 20 mg and about 200 mg per day; between about 30 mg and about 150 mg per day; between about 40 mg and about 90 mg per day; between about 50 mg and about 90 mg per day. Alternatively, in relation to a 60 kg person, in an amount of between about 0.1 mg/kg to about 100 mg/kg per day; between about 0.5 mg/kg and about 80 mg/kg per day, between about 1 mg/kg and about 50 mg/kg per day; between about 1 mg/kg and about 20 mg/kg per day; between about 3 μg/kg and about 50 μg/kg per day. In embodiments, amounts of the ketone body to administer to a human are either 1 mM, 72 mg per day, or 1.2 mg/kg/day.

According to the invention, a methylxanthine includes a methylxanthine that is capable of enhancing autophagy, either alone as a single agent or as part of an inventive combination disclosed herein. Illustrative methylxanthine compounds include caffeine, aminophylline, 3-isobutyl-1-methylxanthine, paraxanthine, pentoxifylline, theobromine, and theophylline.

Accordingly, the amount of the methylxanthine to use includes between about 1% and about 50% of the therapeutic dose as a single agent, or between about 5% and about 50% of the therapeutic dose as a single agent, or between about 10% and about 50% of the therapeutic dose as a single agent, or about 10% of the dose of the therapeutic dose as a single agent. For example, the methylxanthine, in the combination, can be used in a formulation of between about 0.01 μM and about 50 μM; between about 0.1 μM and about 20 μM, between about 0.5 μM and about 5 μM; between about 1 μM and about 2 μM. Alternatively, the methylxanthine can be administered, in a human, at the following dose ranges. The dose ranges are given for caffeine, but one of skill in the art can adjust the dosing for other methylxanthines so the equivalent amount is given. The methylxanthine can be administered at between about 0.1 mg and about 300 mg per day; between about 0.5 mg and about 200 mg per day; between about 1 mg and about 100 mg per day; between about 2 mg and about 50 mg per day; between about 2 mg and about 50 mg per day. Alternatively, in relation to a 60 kg person, in an amount of between about 0.01 mg/kg to about 10 mg/kg per day; between about 0.05 mg/kg and about 5 mg/kg per day, between about 0.1 mg/kg and about 1 mg/kg per day. In embodiments, amounts of the methylxanthine to administer to a human are either 1 mM, 3.2 mg per day, or 0.05 mg/kg/day.

The amount of each compound in the combination to administer and the timing of administration will depend on the type (species, gender, age, weight, smoker/non-smoker, etc.) and condition of the patient being treated, the severity of the disease or condition being treated, and on the route of administration. For example, compounds can be administered to a patient in doses ranging from 0.001 to 10,000 mg/kg of body weight per day or per week in single or divided doses, or by continuous infusion.

In one embodiment, the present invention includes wherein the combination and/or composition comprises a saccharide, a vitamin, and a ketone body. In one embodiment, the saccharide is trehalose, the vitamin is cholecalciferol, and the ketone body is β-hydroxybutyrate. In one embodiment, the patient is human, and the trehalose is administered in a dose of about 2 or 4 g per day or about 33 or 66 mg/kg/day; the cholecalciferol is administered in a dose of about 1.6 μg per day or about 26 ng/kg/day; and the β-hydroxybutyrate is administered in a dose of about 72 mg per day or about 1.2 mg/kg/day.

In one embodiment, the present invention includes wherein the combination and/or composition comprises a saccharide, a vitamin, and a polyphenol. In one embodiment, the saccharide is trehalose, the vitamin is cholecalciferol, and the polyphenol is epigallocatechin gallate. In one embodiment, the patient is human, and the trehalose is administered in a dose of about 2 or 4 g per day or about 33 or 66 mg/kg/day; the cholecalciferol is administered in a dose of about 1.6 μg per day or about 26 ng/kg/day; and the epigallocatechin gallate is administered in a dose of about 3.2 mg per day or about 0.05 mg/kg/day.

In one embodiment, the present invention includes wherein the combination and/or composition comprises a methylxanthine, a polyphenol, and a ketone body. In one embodiment, the methylxanthine is caffeine, the polyphenol is epigallocatechin gallate, and the ketone body is β-hydroxybutyrate. In one embodiment, the patient is human, and the caffeine is administered in a dose of about 3.2 g per day or about 0.05 mg/kg/day; the epigallocatechin gallate is administered in a dose of about 240 μg per day or about 0.004 mg/kg/day; and the β-hydroxybutyrate is administered in a dose of about 72 mg per day or about 1.2 mg/kg/day.

In one embodiment, each compound in the composition may be administered in either a therapeutic or subtherapeutic amount (according to single agent dosage) for the treatment of a condition associated with reduced autophagy. Therapeutic amounts of each compound in the composition, as a single agent, may also be used.

The treatment regimen, in one embodiment, can be for any length of time as determined is effective, and may be 1 day or more, 2 days or more, 3 days or more, 4 days or more, 5 days or more, 10 days or more, 15 days or more, 20 days or more, 25 days or more, 30 days or more, 35 days or more, 40 days or more; or one week or more, two weeks or more, three weeks or more, a month or more, two months or more, three months or more, four months or more, six months or more, or unlimited duration.

The compounds of the combinations disclosed herein may be administered simultaneously, separately or sequentially. Preferably the compounds that are independently selected from at least two of the groups disclosed herein are administered within 6 hours, more preferably 4 hours, more preferably 2 hours of one another. In one embodiment the compounds are administered simultaneously. For example the two drugs may be administered simultaneously by oral administration.

For purposes of the present invention, when administered simultaneously, such administration may also be termed "co-administration of" and "co-administering" the compounds of the combination, and may refer to any administration of the compounds, either separately or together, where the compounds are administered as part of an appropriate dose regimen designed to obtain the benefit of the combination therapy. Thus, the compounds can be administered either as part of the same pharmaceutical composition or in separate pharmaceutical compositions. Each compound can be administered prior to, at the same time as, or subsequent to administration of another compound in the combination, or in some combination thereof. Where one compound is administered to the patient at repeated intervals, the other compound(s) can be administered prior to, at the same time as, or subsequent to, each administration of the first compound, or some combination thereof, or at different intervals in relation to the first compound, or in a single dose prior to, at any time during, or subsequent to the course of treatment with the first compound.

The combinations and compositions of the invention will typically be administered to the patient in a dose regimen that provides for the most effective treatment of the condition or disease associated with reduced autophagy (from both efficacy and safety perspectives) for which the patient is being treated, as known in the art, and as disclosed herein. In conducting the treatment method of the present invention, the compounds in the combination or composition can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of condition being treated, the type of compound being used, and the medical judgement of the prescribing physician as based, e.g., on the results of published clinical studies.

A "patient" or "subject" to be treated by the compositions and/or combinations of the present invention include a human patient or a non-human patient, such as a non-human primate, a companion animal, a food animal, for example.

The compounds of the inventive compositions and/or combinations can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

Methods of preparing pharmaceutical compositions comprising a compound of the invention are known in the art, including known references, such as Remington's Pharmaceutical Sciences, Mack Publishing Company, Easton, Pa., 18th edition (1990). The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

For oral administration of the inventive combinations and/or compositions, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the combinations and compositions may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of the compounds and compositions of the invention, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

For veterinary purposes, the active agents can be administered separately or together to animals using any of the forms and by any of the routes described above. In a one embodiment, in the form of a capsule, bolus, tablet, liquid drench, by injection or as an implant. As an alternative, the inventive compositions and/or combinations can be administered with the animal feedstuff, and for this purpose a concentrated feed additive or premix may be prepared for a normal animal feed. Such formulations are prepared in a conventional manner in accordance with standard veterinary practice.

Any of the compounds named herein may be present in the form of a pharmaceutically acceptable salt. The term "pharmaceutically acceptable salt" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When a compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient.

The present invention further provides a kit comprising a single container comprising both an EGFR kinase inhibitor and PDX. The present invention further provides a kit comprising a first container comprising an EGFR kinase inhibitor and a second container comprising PDX. In a preferred embodiment, the kit containers may further include a pharmaceutically acceptable carrier. The kit may further include a sterile diluent, which is preferably stored in a separate additional container. The kit may further include a package insert comprising printed instructions directing the use of the combined treatment as a method for treating cancer.

EXAMPLES

Example 1: A Novel Nutraceutical for Improving Physiological Function with Age

Introduction

Aging causes numerous adverse changes in physiology, including arterial dysfunction, reduced motor function (strength, locomotion, etc.) and impaired liver/metabolic function. Collectively, these changes reduce independence and quality of life and predispose older adults to disabilities and chronic diseases [1]. Because the number of older adults in the US is expected to more than double by 2050, age-related physiological dysfunction (and resulting diseases/disabilities) are expected to cause major socio-economic problems in the near future [2, 3]. Identifying novel therapies that improve physiological function with aging is, therefore, an important biomedical research objective.

Because aging is a complex process with numerous physiological consequences, agents that target fundamental "upstream" causes of aging (rather than treating isolated late-life pathologies as pharmaceuticals do) may have the greatest probability of reversing dysfunction and preventing the development of disease [4, 5]. In this context, autophagy is a particularly promising target [6]. Autophagy is the major cellular process for recycling damaged proteins and organelles, and it protects many cellular and systemic physiological functions against aging and disease [7]. Impaired autophagy is implicated in numerous age-related disorders- including vascular dysfunction [8], impaired motor (neuromuscular) function [9] and altered liver structure/function [10]-all of which contribute significantly to disability and disease. Thus, the development of autophagy-enhancing therapies is a compelling direction for research aimed at preventing/treating disorders of aging.

Unfortunately, many pharmacological autophagy inducers have off-target effects (e.g., rapamycin) [11]. As a result, there is considerable interest in nutraceuticals-naturally occurring, bioactive food compounds—that promote autophagy [12]. We and others have shown that dietary supplementation with autophagy-enhancing nutraceuticals, such as the carbohydrate trehalose, reverses age-related dysfunction [8, 13], but there are limitations to this approach. For example, the amount of trehalose that improves function in mice equates to >500 calories of sugar per day in humans. The same is true for many nutraceuticals; the concentrations needed for beneficial effects are often supraphysiological [14]. Thus, the aim of the present study was to achieve effects similar to trehalose and other autophagy inducers without the associated limitations by developing an autophagy-enhancing optimized nutraceutical (AEON)—a formulation of naturally occurring dietary compounds that enhances autophagy via the synergistic action of low doses of its ingredients. To do so, we conducted a series of in vitro screening experiments to identify combinations of nutraceutical compounds that synergistically induce autophagy. Then, we developed promising combinations into FDA-approvable food supplements and tested them in vivo in a mouse model of physiological aging.

Experimental Section

Materials and Methods.

First, we compiled a library of naturally occurring compounds known to enhance autophagy [15-19]. Then, we calculated physiologically relevant concentrations of these compounds based on existing data (e.g., previously reported post-prandial plasma concentrations), and we tested each for its ability to induce autophagy at its calculated concentration alone and/or in combination with other candidate compounds. For each binary combination that significantly stimulated autophagy, individual components were further examined for their ability to induce autophagy synergistically in tertiary combinations. In all experiments, autophagy was assessed in human umbilical vein endothelial cells (HUVEC), because of their relevance to vascular physiological measures (in vivo measures, below) [8]. Pooled HUVEC cultures obtained from Cascade Biologics were grown in endothelial cell-specific medium (Lonza) at 37° C. in a 5% humidity incubator. Third passage cells were seeded into 96-well plates and allowed to reach 70% confluency, at which point candidate treatment compounds or combinations were applied for 24 hours. Cells were observed for viability, and treatments that caused significant cell death and/or morphological changes were excluded from further study. Autophagy was assessed using Enzo Life Sciences Cyto-ID autophagy detection reagents (fluorescence microplate detection of autophagic structures) according to manufacturers instructions on an M5 Spectramax fluorescent plate reader (Molecular Devices) [20, 21]. Candidate AEON formulations were designated as AEON-1, -2, etc.

In Vivo AEON Treatments

To maximize relevance and potential translation to humans, candidate AEON formulations that significantly stimulated autophagy in vitro were evaluated for their potential to be translated into FDA-approvable, food-based supplements for mouse (and human) studies, and viable formulations were further developed using proprietary techniques by Renutris Scientific (Boulder, CO). Briefly, FDA-approved food ingredients containing bioavailable forms of AEON constituent compounds were identified and purchased from established manufacturers (BASF, ADM, OHM, Cargill, etc.) and combined in sufficient amounts to achieve mouse doses proportional to calculated physiologically relevant levels in humans (i.e., on a per kilogram body weight basis, adjusted for differences in metabolism). For administration to mice, supplements were prepared as gelatin drops by dissolving ingredients in heated solutions containing varying concentrations of gelatin and food flavoring (Flavorganics), as well as appropriate preservatives, pipetting a calculated volume (for one dose/mouse) into individual wells of a pre-fabricated plastic mold and allowing it to cool overnight-all under sterile conditions. Shelf life/stability of each mixture was tested by assessing physical condition, pH, bacterial/mold growth and composition using commercially available kits as applicable. Stable formulations were presented to mice on a randomized basis to determine flavor/density preferences (i.e., what flavor/strength and texture mice would eat voluntarily). Viable AEON food supplement formulations were designated as AEON-1f, -2f, etc.

Young (4 months) and old (27 months, ~50% survival rate) male C57Bl6 mice were obtained from the National Institute on Aging mouse colony. Mice were housed in an animal care facility at the University of Colorado at Boulder on a 12:12 h light-dark cycle. All procedures conformed to the Guide for the Care and Use of Laboratory Animals (NIH publication no. 85-23, revised 2011) and were approved by the University of Colorado at Boulder Animal Care and Use Committee. Gelatin drops (FIG. 2) were administered to mice at the same time each day on small plastic weigh boats, and animals were monitored to ensure that the entire supplement was eaten. Control animals received isocaloric "vehicle" drops (gelatin and flavor only). All treatments were administered for a total of 30 days.

In Vivo Measures of Physiological Function

Indices of vascular, motor and liver function were assessed in young and old mice supplemented with candidate AEON formulations or vehicle (control) treatments. All mice were assessed for the following physiological indicators of age-related dysfunction: vascular dysfunction—increased arterial stiffness and reduced arterial endothelial function, which increase the risk for cardiovascular diseases and contribute to reduced functional capacity [22]; impaired motor (neuromuscular) function—reduced endurance, muscle strength and coordination, which reduce functional capacity and increase the risk of falls and disability [23]; and altered liver structure/function-increased cellular damage, which impairs the ability to respond to metabolic and other hepatic insults and increases the risk of liver diseases [24].

Vascular function was measured as previously described [8, 13, 25]. Arterial stiffness: aortic pulse wave velocity (aP\M/) was measured pre/post-treatment as described previously. Mice were anesthetized and placed on a heating board with legs secured to ECG electrodes, and velocity at the transverse aortic arch and abdominal aorta was measured with a Doppler probe. Time between the ECG R-wave and the Doppler signal were determined for each site, and aP\M/was calculated as the distance between sites divided by the difference in time elapsed at each site. Arterial endothelial function: endothelium-dependent dilation (EDD) was assessed post-treatment ex vivo in carotid arteries as described previously. Mice were sacrificed by cardiac puncture/exsanguination, and arteries were isolated and cannulated onto glass micropipettes in myograph chambers. After equilibration/preconstriction, EDD was determined by measuring increases in luminal diameter to the cumulative addition of acetylcholine.

Motor function was assessed by a behavioral battery (Table 1) that measures locomotion, strength, balance and endurance using tests described in detail previously [26]. These tests are aligned with those comprising the Motor Function Domain of the NIH Toolbox, a new set of standardized measures in humans [27].

TABLE 1

Motor Function Battery: Description of Individual Tests

| | Test | Measurement Detail |
|---|---|---|
| Strength | Grip strength | Force at release of forepaw grip; Force normalized to body mass |
| Endurance | Tightrope hang | Maximal time achieved suspended by forepaws from taught string |
| | Endurance Run | Distance run on a rota-rod speeds equivalent to 75% and 100% max |
| Locomotion | Walk Speed | Average speed to traverse an 80 cm straight walking track |
| | Rearing Count | Number of rears over 3-min exposure to 12.5 cm rearing cylinder |
| | Open Field Distance | Distance traveled during 5-min exposure to a novel open field |
| Balance/ Coordination | Accelerating Rota-Rod | Average latency to fall from an accelerating rotating rod |

Liver injury/stress was assessed by measuring the established liver damage/stress markers alanine and aspartate aminotransferases (ALT and AST) as described previously using conventional commercial kits according to manufacturers' instructions (ALT: Cayman Chemical, AST: Sigma) [28, 29].

Animal Model Predictive Indication

The following references provide description illustrating predictive use of the animal model results as for treatment of humans:

Pulse wave velocity predicts cardiovascular disease/mortality: Ben-Shlomo, Yoav, et al. "Aortic pulse wave velocity improves cardiovascular event prediction: an individual participant meta-analysis of prospective observational data from 17,635 subjects." Journal of the American College of Cardiology 63.7 (2014): 636-646.

General locomotion measures predict mortality: de Brito, Leonardo Barbosa Barreto, et al. "Ability to sit and rise from the floor as a predictor of all-cause mortality." European journal of preventive cardiology 21.7 (2014): 892-898.

Strength predicts mortality: Sasaki, Hideo, et al. "Grip strength predicts cause-specific mortality in middle-aged and elderly persons." The American journal of medicine 120.4 (2007): 337-342.

Endurance predicts mortality: Sui, Xuemei, et al. "Estimated functional capacity predicts mortality in older adults." Journal of the American Geriatrics Society 55.12 (2007): 1940-1947.

Results and Discussion

Proof of Concept and Identification of Candidate AEON Formulations

Figure 1B:
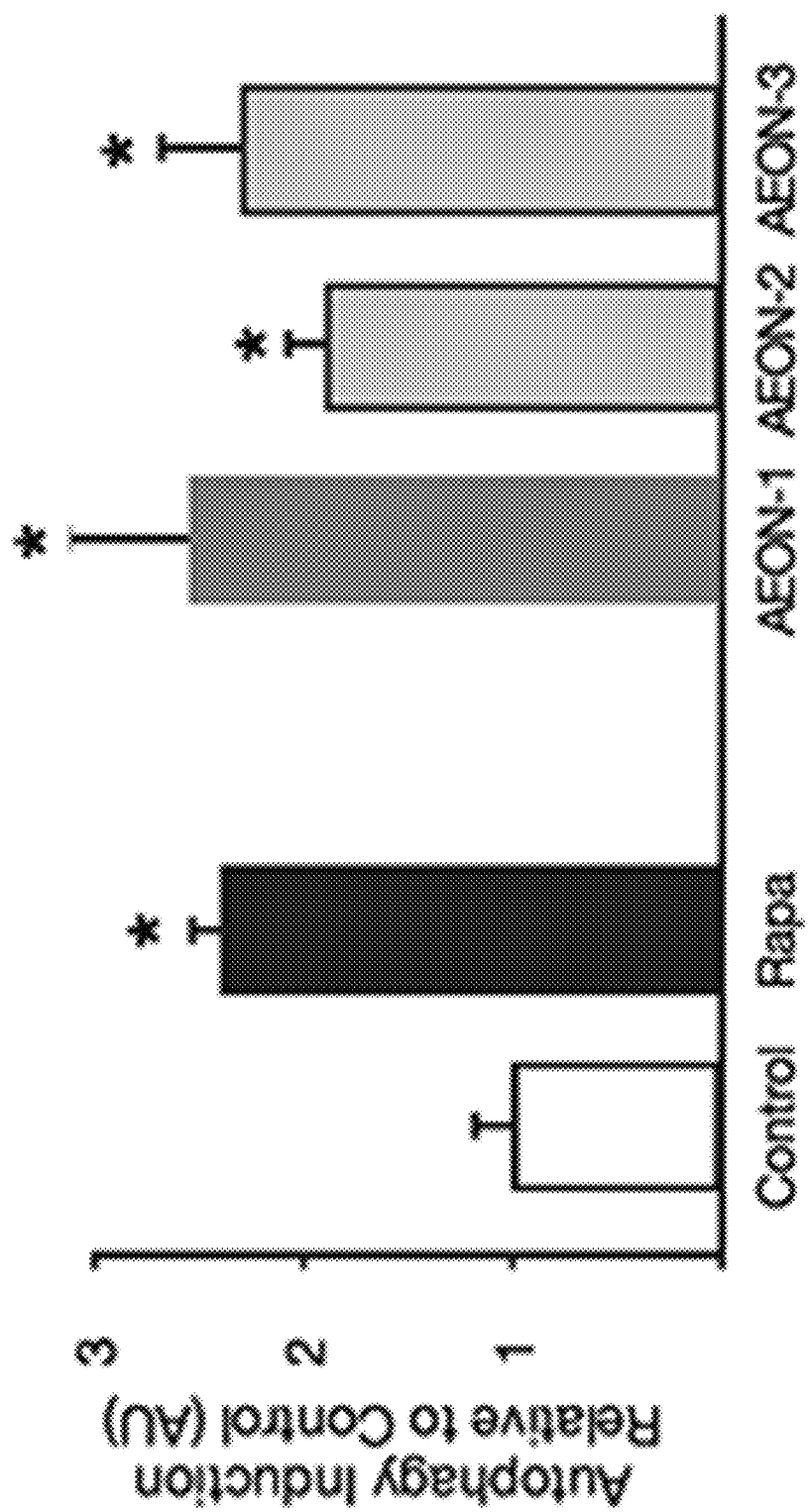
FIG. 1B. Three formulations of AEON that stimulate autophagy comparably to rapamycin and high dose trehalose. *P<0.05 vs. control, assessed by ANOVA and Tukey post-hoc tests. N=5 trials per group.

The established autophagy inducers rapamycin (0.5 µM) and trehalose (50 mM—the concentration used in our previous aging studies in mice) significantly stimulated autophagy in HUVEC (FIG. 1A). In contrast, low (physiologically relevant) doses of nutraceuticals such as trehalose (5 mM) and the ingredients trehalose alone, cholecalciferol alone, and epigallocatechin gallate alone had no effect on autophagy. However, when trehalose, cholecalciferol, and epigallocatechin gallate were combined as AEON-1, they stimulated autophagy comparably to rapamycin and high dose trehalose (FIG. 1A). Co-incubation with the autophagy blocker 3-MA prevented this effect. By subjecting our library of naturally occurring compounds known to enhance autophagy to similar combinatorial screening experiments, we identified three similar candidate AEON formulations that synergistically activate autophagy. These formulations, dubbed AEON-1, -2 and -3, recipe provided below, stimulated autophagy comparably to rapamycin and trehalose (FIG. 1B). Taken together, these data suggest that it is possible to synergistically stimulate autophagy using nutraceutical compounds.

Formulation of Safe/Stable AEON Food Supplements

Figure 2:
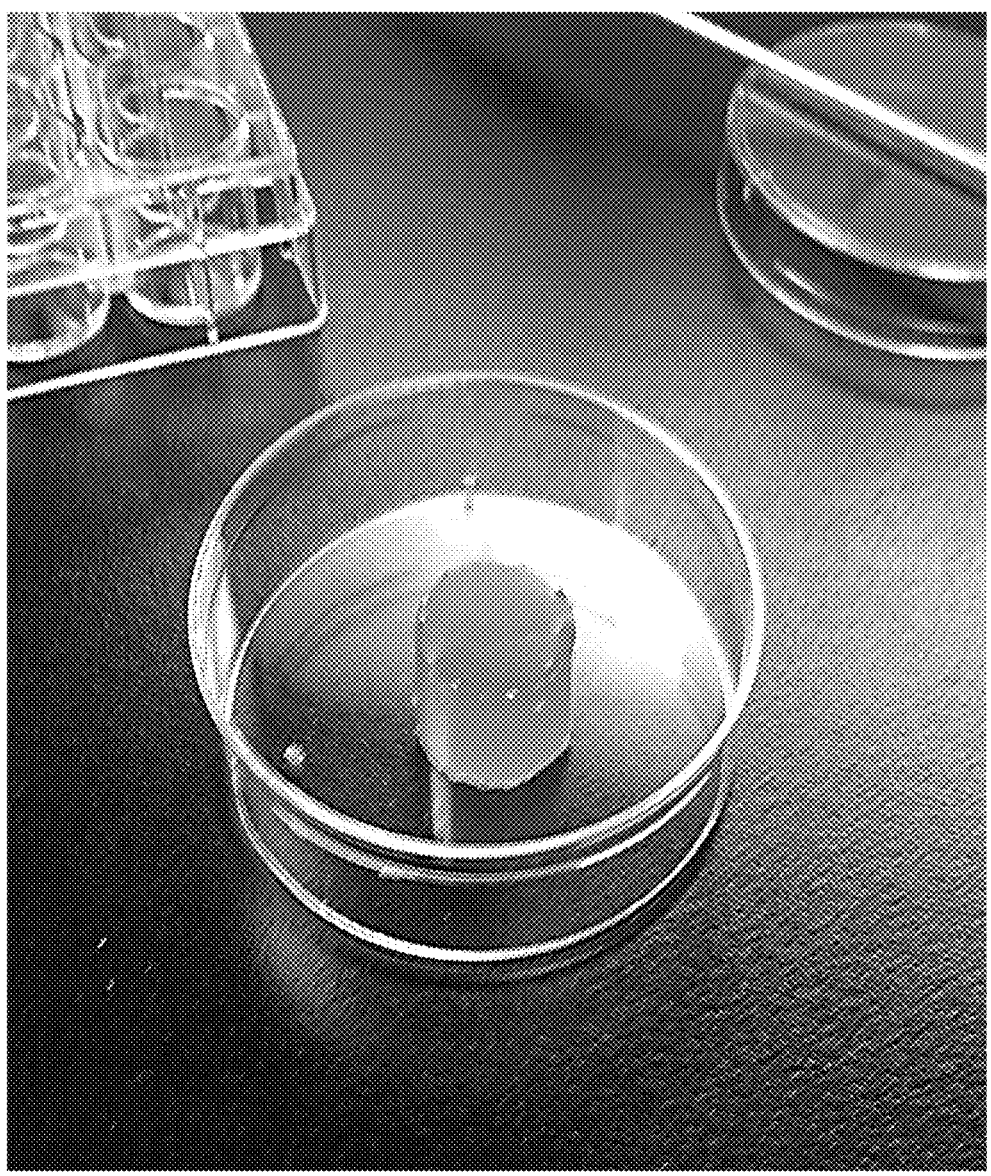
FIG. 2. Representation of "gumdrop" formulation.
Figure 3A:
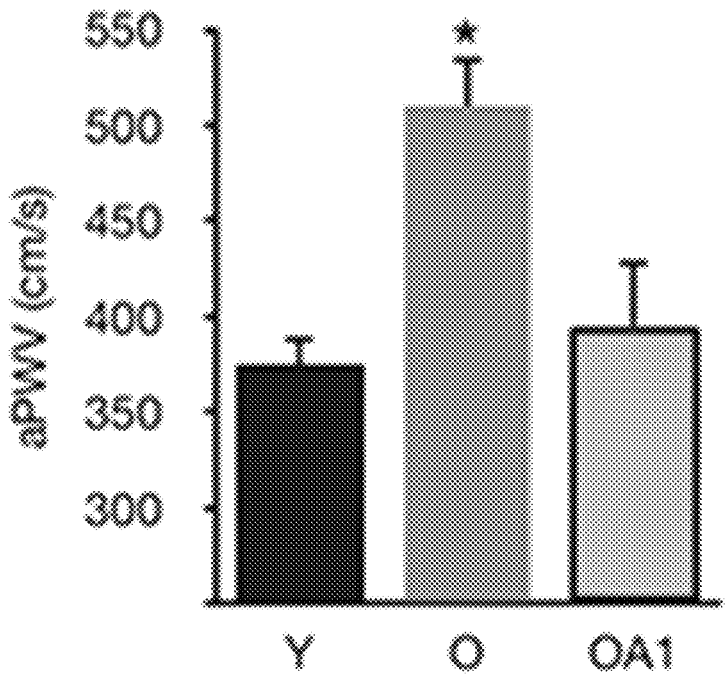
FIG. 3A. Aortic pulse wave velocity (aPWV, arterial stiffness) in young (Y) and old (O) control mice and old mice supplemented for 30 days with AEON-1f (OA1). *P<0.05 vs. young assessed by ANOVA and Tukey post-hoc tests. N=7-8 animals per group.
Figure 3B:
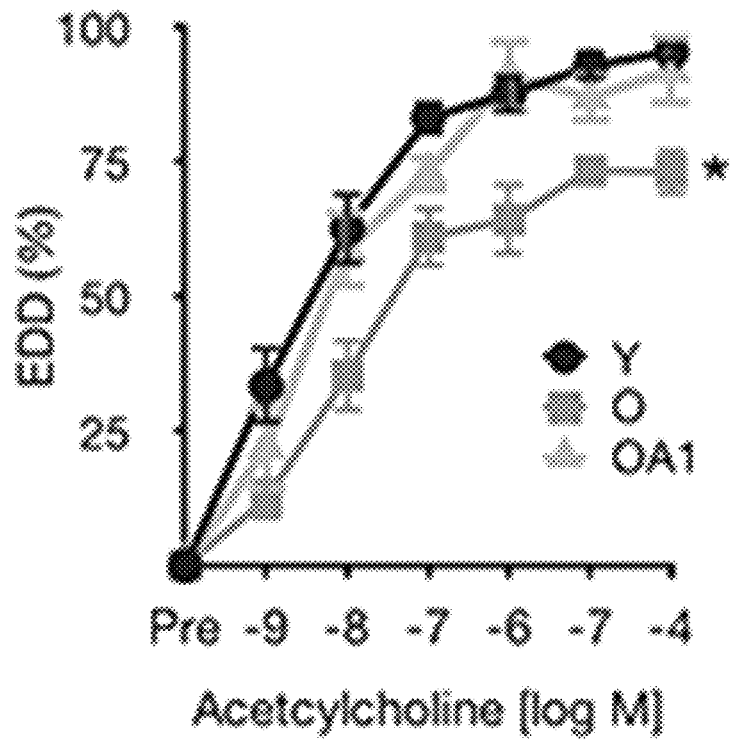
FIG. 3B. Carotid artery endothelium-dependent dilation (EDD) in response to acetylcholine in young (Y) and old (O) control mice and old mice supplemented for 30 days with AEON-1f (OA1). *P<0.05 vs. young assessed by ANOVA and Tukey post-hoc tests. N=7-8 animals per group.
Figure 3C:
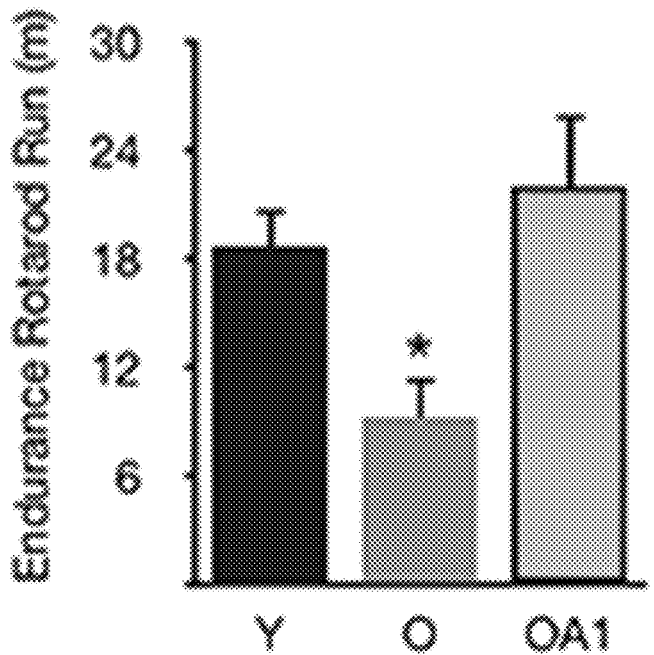
FIG. 3C. Endurance rotarod performance (distance) in young (Y) and old (O) control mice and old mice supplemented for 30 days with AEON-1f (OA1). *P<0.05 vs. young assessed by ANOVA and Tukey post-hoc tests. N=7-8 animals per group.
Figure 3D:
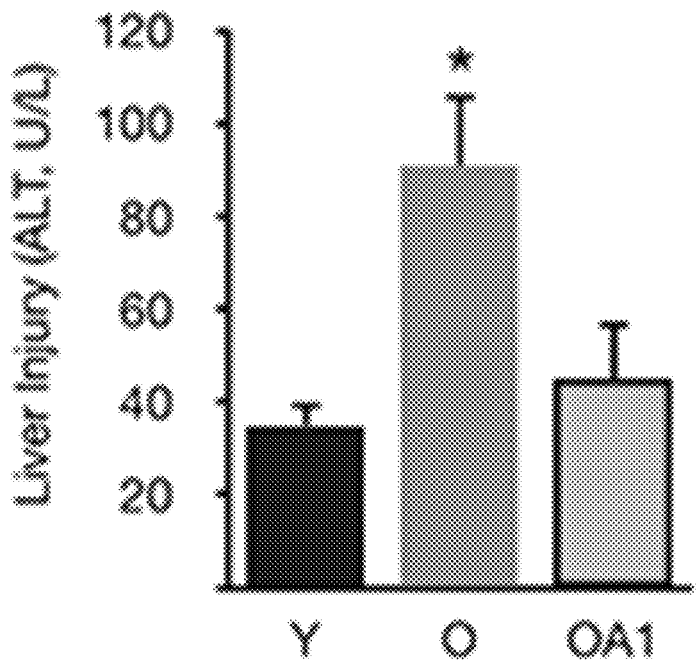
FIG. 3D. Liver injury/damage as indicated by alanine amino-transferase (ALT) in young (Y) and old (O) control mice and old mice supplemented for 30 days with AEON-1f (OA1). *P<0.05 vs. young assessed by ANOVA and Tukey post-hoc tests. N=7-8 animals per group.

AEON "gum drops" prepared under sterile conditions in a 10% gelatin solution and stored at 4° C. for 5 days displayed the greatest long-term stability and no mold/bacterial growth. Mice showed a distinct preference for drops prepared from ingredients combined with 2% chocolate flavor. In general, old mice were more averse to the presentation of novel food, but given ~15 min of undisturbed time with 10% gelatin, 2% gelatin drops, all mice eventually ate the treatments voluntarily. Therefore, all subsequent AEON-f supplements were prepared using similar solutions and flavorings (FIG. 2).

In Vivo Measures of Physiological Function

From the candidate AEON formulations identified via in vitro screening experiments and translated into food supplement form, we identified AEON-1f as having significant effects on age-related physiological dysfunction in vivo. Old control mice had increased arterial stiffness (aPWV), reduced arterial endothelial function (EDD), impaired motor function (indicated by reduced rota-rod endurance time) and elevated markers of liver damage/injury (ALT) compared with young animals (FIG. 3A-D). However, supplementing old mice with AEON-1f for 30 days reversed these age-related impairments.

Conclusions

The key findings of the present study are that: 1) certain combinations of nutraceutical compounds have the potential to synergistically enhance autophagy; and 2) at least one of these combinations, when translated into a safe/stable food supplement (AEON-1f), has the potential to significantly improve multiple physiological functions in old mice. These findings are clinically relevant, as age-related physiological dysfunction (as indicated by increased arterial stiffness, reduced arterial endothelial function, impaired motor performance and liver injury/dysfunction) is a powerful predictor of disease and disability in older adults [1, 23, 24, 30, 31].

After lifestyle modifications, which many older adults cannot/will not adopt, pharmacological strategies are the traditional second defense against age-associated dysfunction and disease. However, while pharmaceuticals may address some age-related disorders, their development is slow and costly, and they are often associated with unwanted side effects [4]. Certain dietary supplements also may ameliorate dysfunction, but most commercially available supplements and nutraceuticals are based on limited or no scientific evidence-largely because the costs, expertise and logistical challenges of validating such therapies are prohibitive [32].

Autophagy has significant health-promoting potential as an upstream anti-aging process with the ability to prevent/reverse the effects of aging at multiple levels [6, 7]. However, most established autophagy enhancers (e.g., pharmacological inducers, dietary interventions) are also associated with numerous drawbacks [11]. Thus, our invention (AEON-1f) has promising translational potential, because it: 1) enhances autophagy via the synergistic action of physiologically relevant (low) concentrations of natural food ingredients; 2) is made from safe/accessible FDA-approved food ingredients; and 3) significantly improves multiple indices of physiological function (vascular, motor and liver) with aging.

Collectively, our novel findings suggest that AEON-1f may have strong potential as a unique, diet-based strategy for improving health (physiological function) and reducing disease risk. The exact mechanisms by which AEON-1f activates autophagy (i.e., cell signaling pathways) and improves physiological function remain to be determined, but the present study provides an experimental basis for future investigations of AEON-1f (and other synergistic nutraceutical autophagy-enhancers) in animal models of age-related dysfunction and disease. Moreover, because AEON-1f is composed of FDA-approved, naturally-occurring ingredients that are safe for human consumption, our experiments may serve as a platform for a clinical trial to examine the effects of AEON-1f on physiological function and disease risk in older adults.

Example 2

To identify a mixture of food-safe compounds that synergistically activates autophagy (the cellular process of recycling damaged internal components), we screened a library of natural compounds reported to induce autophagy in vitro (in cells). We were able to identify several potential formulations for an autophagy-enhancing optimized nutraceutical (AEON), as follows: Paradigm for identification of AEON formulations: The ingredients alone have no effect on autophagy in cultured cells, but when combined as AEON-1, they stimulate autophagy similarly to rapamycin (an established pharmacological autophagy inducer). Autophagy was assessed via fluorescent microplate assay and confirmed by microscopy in cultured human umbilical vein endothelial cells treated for 24 hours.

Identification of Several Candidate AEON Formulations:

Through parallel experiments, we identified several AEON formulations that stimulate autophagy similarly to rapamycin via the synergistic action of low-concentration natural compounds that are either: 1) available as FDA-approved food ingredients, or 2) bioavailable at sufficient concentrations in standard FDA-approved food ingredients. The specific compositions (X, Y and Z components) of the formulations are as follows:

AEON-1: 5 mM trehalose, 2 nM cholecalciferol, 1 μM epigallocatechin gallate
AEON-2: 10 mM trehalose, 2 nM cholecalciferol, 1 mM β-hydroxybutyrate
AEON-3: 20 μM caffeine, 1 μM epigallocatechin gallate, 1 mM 3-hydroxybutyrate Novelty of the invention: Each of the individual ingredients above has been reported to induce autophagy at concentrations ~10 times greater than those listed. Extrapolation/translation of such doses of these individual compounds to humans is impossible. Trehalose, for example, induces autophagy in cells and mice at 50-100 mM concentrations. Extrapolated to humans (based on mice drinking ~5 ml trehalose-supplemented water per day), this equates to 100-200 g trehalose—or ~400-800 calories of sugar per day on a per kg body weight basis—an impractical dose. Similarly, caffeine, reported to induce autophagy at 1-20 mM concentrations, cannot be administered as such to enhance autophagy in humans (or mice), as these concentrations are roughly ~100-fold greater than plasma (blood) levels achieved by drinking several cups of coffee. Thus, we believe that one or more of the AEON formulations listed above may be a viable base formulation for a food-based autophagy inducer, providing that: 1) the ingredients can be combined into a stable, FDA-approvable form, and 2) a version that demonstrates efficacy in vivo can be identified.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

1. Kirkland, J. L., *Translating advances from the basic biology of aging into clinical application*. Experimental Gerontology, 2013. 48(1): p. 1-5.
2. Olshansky, S. J., et al., *Aging in America in the twenty-first century: demographic forecasts from the MacArthur Foundation Research Network on an Aging Society*. Milbank Q, 2009. 87(4): p. 842-62.
3. Lunenfeld, B. and P. Stratton, *The clinical consequences of an ageing world and preventive strategies*. Best Practice & Research Clinical Obstetrics & Gynaecology, 2013: p. 1-17.
4. Larrick, J. W. and A. Mendelsohn, *Applied Healthspan engineering*. Rejuvenation Research, 2010. 13(2-3): p. 265-280.
5. Ingram, D. K., et al., *Calorie restriction mimetics: an emerging research field*. Aging Cell, 2006. 5(2): p. 97-108.
6. Rubinsztein, D. C., G. Marino, and G. Kroemer, *Autophagy and Aging*. Cell, 2011. 146(5): p. 682-695.
7. Mizushima, N. and M. Komatsu, *Autophagy: Renovation of Cells and Tissues*. Cell, 2011. 147(4): p. 728-741.
8. LaRocca, T. J., et al., *Translational evidence that impaired autophagy contributes to arterial ageing*. The Journal of Physiology, 2012. 590(14): p. 3305-3316.
9. Wohlgemuth, S. E., et al., *Skeletal muscle autophagy and apoptosis during aging: Effects of calorie restriction and life-long exercise*. Experimental Gerontology, 2010. 45(2): p. 138-148.
10. Zhang, C. and A. M. Cuervo, *Restoration of chaperone-mediated autophagy in aging liver improves cellular maintenance and hepatic function*. Nature Medicine, 2008. 14(9): p. 959-965.
11. Sudarsanam, S. and D. E. Johnson, *Functional consequences of mTOR inhibition*. Curr Opin Drug Discov Devel, 2010. 13(1): p. 31-40.
12. Galluzzi, L. and G. Kroemer, *Autophagy Mediates the Metabolic Benefits of Endurance Training*. Circulation Research, 2012. 110(10): p. 1276-1278.
13. Larocca, T. J., et al., *The autophagy enhancer spermidine reverses arterial aging*. Mech Ageing Dev, 2013. 134(7-8): p. 314-20.
14. Nicoletti, M., *Nutraceuticals and botanicals: overview and perspectives*. International Journal of Food Sciences and Nutrition, 2012. 63(S1): p. 2-6.
15. Pietrocola, F., et al., *Pro-autophagic polyphenols reduce the acetylation of cytoplasmic proteins*. Cell Cycle, 2012. 11(20).
16. Pallauf, K. and G. Rimbach, *Autophagy, polyphenols and healthy ageing*. Ageing Res Rev, 2012. 12(1): p. 237-252.
17. Ferrari, N., et al., *Diet-derived phytochemicals: from cancerchemoprevention to cardio-oncological prevention*. Current drug targets, 2011. 12(13): p. 1909-1924.
18. Hannigan, A. M. and S. M. Gorski, *Macroautophagy: the key ingredient to a healthy diet?* Autophagy, 2009. 5(2): p. 140-51.
19. Singletary, K. and J. Milner, *Diet, autophagy, and cancer: a review*. Cancer epidemiology, biomarkers & prevention: a publication of the American Association for Cancer Research, cosponsored by the American Society of Preventive Oncology, 2008. 17(7): p. 1596-1610.
20. Pandit, B. and A. L. Gartel, *FoxM1 knockdown sensitizes human cancer cells to proteasome inhibitor-induced apoptosis but not to autophagy*. Cell Cycle, 2011. 10(19): p. 3269-73.
21. Chan, L. L., et al., *A novel image-based cytometry method for autophagy detection in living cells*. Autophagy, 2012. 8(9): p. 1371-82.
22. Lakatta, E. G. and D. Levy, *Arterial and cardiac aging: major shareholders in cardiovascular disease enterprises: Part I: aging arteries: a "set up" for vascular disease*. Circulation, 2003. 107(1): p. 139-46.
23. Cooper, R., et al., *Objective measures of physical capability and subsequent health: a systematic review*. Age Ageing, 2011. 40(1): p. 14-23.
24. Sheedfar, F., et al., *Liver diseases and aging: friends or foes?* Aging Cell, 2013.
25. Fleenor, B. S., et al., *Superoxide-lowering therapy with TEMPOL reverses arterial dysfunction with aging in mice*. Aging Cell, 2012. 11(2): p. 269-276.
26. Justice, J. N., et al., *Battery of behavioral tests in mice that models age-associated changes in human motor function*. Age (Dordr), 2013.
27. Reuben, D. B., et al., *Motor assessment using the NIH Toolbox*. Neurology, 2013. 80(11 Suppl 3): p. S65-75.
28. Gregg, S. Q., et al., *A mouse model of accelerated liver aging caused by a defect in DNA repair*. Hepatology, 2012. 55(2): p. 609-21.
29. Fontana, L., et al., *Aging promotes the development of diet-induced murine steatohepatitis but not steatosis*. Hepatology, 2013. 57(3): p. 995-1004.
30. Mitchell, G. F., et al., *Arterial stiffness and cardiovascular events: the Framingham Heart Study*. Circulation, 2010. 121(4): p. 505-511.
31. Seals, D. R., K. L. Jablonski, and A. J. Donato, *Aging and vascular endothelial function in humans*. Clin Sci (Lond), 2011. 120(9): p. 357-75.
32. Galis, Z. S., J. B. Black, and S. I. Skarlatos, *National Heart, Lung, and Blood Institute and the Translation of Cardiovascular Discoveries Into Therapeutic Approaches*. Circulation Research, 2013. 112(9): p. 1212-1218.

We claim:

1. A method for treating a disease or condition associated with reduced autophagy in a human patient, comprising increasing autophagy in cells of said patient by administering to said patient a therapeutically effective amount of a combination consisting of between about 5 mM and about 10 mM trehalose or a pharmaceutically acceptable salt thereof, between about 1 nM and about 10 nM cholecalciferol or a pharmaceutically acceptable salt thereof, between about 0.5 M and about 5 UM epigallocatechin gallate or a pharmaceutically acceptable salt thereof, and optionally between about 0.5 μM and about 5 μM of a methylxanthine compound or a pharmaceutically acceptable salt thereof, and optionally a pharmaceutical carrier,
    wherein the trehalose or pharmaceutically acceptable salt thereof is administered in a total amount of about 1 to about 200 mg/kg of body weight of the patient per day, the cholecalciferol or pharmaceutically acceptable salt thereof is administered in a total amount of about 1 ng/kg to about 500 ng/kg of body weight of the patient per day, the epigallocatechin gallate or pharmaceutically acceptable salt thereof is administered in a total amount of about 0.5 μg/kg to about 300 μg/kg of body weight of the patient per day, and optionally the methylxanthine compound or pharmaceutically acceptable salt thereof is administered in a total amount of about 0.01 to about 10 mg/kg of body weight of the patient per day,
    wherein the combination has a synergistic autophagy enhancement effect and increases autophagy in the cells of said patient by at least 10% as compared to the level of autophagy present in an untreated cell or a cell treated with a placebo.

2. The method of claim 1, wherein the methylxanthine compound is selected from the group consisting of caffeine, aminophylline, 3-isobutyl-1-methylxanthine (IBMX), paraxanthine, pentoxifylline, theobromine, and theophylline.

3. The method of claim 1, wherein the trehalose or pharmaceutically acceptable salt thereof is administered in a total amount of about 20 to about 80 mg/kg of body weight of the patient per day,
    the cholecalciferol or pharmaceutically acceptable salt thereof is administered in a total amount of about 20 to about 100 ng/kg of body weight of the patient per day, and
    the epigallocatechin gallate or pharmaceutically acceptable salt thereof is administered in a total amount of about 2 to about 100 μg/kg of body weight of the patient per day.

4. The method of claim 1, wherein the disease or condition associated with reduced autophagy is aging, cardiovascular disease, neurodegenerative disease, or inflammatory disease.

5. The method of claim 1, wherein the disease or condition associated with reduced autophagy is aging.

6. The method of claim 1, comprising increasing a ratio of LC3-II protein to LC3-I protein in the cells of said patient.

7. The method of claim 1, wherein autophagy in the cells of said patient is increased by at least 50% as compared to the level of autophagy present in an untreated cell or a cell treated with a placebo.

8. The method of claim 1, wherein the disease or condition associated with reduced autophagy is cardiovascular disease.

9. A method for treating a chronic human disease in a human patient, comprising increasing autophagy in cells of said patient by administering to said patient a therapeutically effective amount of a combination consisting of trehalose or a pharmaceutically acceptable salt thereof, cholecalciferol or a pharmaceutically acceptable salt thereof, epigallocatechin gallate or a pharmaceutically acceptable salt thereof, and a methylxanthine compound or a pharmaceutically acceptable salt thereof,
    wherein the trehalose or pharmaceutically acceptable salt thereof is administered in a total amount of about 1 to about 200 mg/kg of body weight of the patient per day, the cholecalciferol or pharmaceutically acceptable salt thereof is administered in a total amount of about 1 ng/kg to about 500 ng/kg of body weight of the patient per day, the epigallocatechin gallate or pharmaceutically acceptable salt thereof is administered in a total amount of about 0.5 μg/kg to about 300 μg/kg of body weight of the patient per day, and the methylxanthine compound or pharmaceutically acceptable salt thereof is administered in a total amount of about 0.01 to about 10 mg/kg of body weight of the patient per day,
    wherein the combination increases autophagy in the cells of said patient by at least 10% as compared to the level of autophagy present in an untreated cell or a cell treated with a placebo and has a synergistic treatment effect for said chronic human disease, and
    wherein the methylxanthine compound is selected from the group consisting of caffeine, aminophylline, 3-isobutyl-1-methylxanthine (IBMX), paraxanthine, pentoxifylline, theobromine, and theophylline.

10. The method of claim 9, wherein the chronic human disease is selected from the group consisting of a cardiovascular disease, cancer, Type 2 diabetes, Alzheimer's disease, Parkinson's disease, rheumatoid arthritis, psoriasis, and multiple sclerosis.

11. The method of claim 9, wherein autophagy in the cells of said patient is increased by at least 50% as compared to the level of autophagy present in an untreated cell or a cell treated with a placebo.

12. The method of claim 9, wherein the trehalose or pharmaceutically acceptable salt thereof is administered in a total amount of about 20 to about 80 mg/kg of body weight of the patient per day,
    the cholecalciferol or pharmaceutically acceptable salt thereof is administered in a total amount of about 20 to about 100 ng/kg of body weight of the patient per day,
    the epigallocatechin gallate or pharmaceutically acceptable salt thereof is administered in a total amount of about 2 to about 100 μg/kg of body weight of the patient per day, and the methylxanthine compound or pharmaceutically acceptable salt thereof is administered in a total amount of about 0.01 to about 0.5 mg/kg of body weight of the patient per day.

13. The method of claim 9, wherein the chronic human disease is cardiovascular disease.

\* \* \* \* \*